United States Patent [19]

Hara et al.

[11] Patent Number: 4,767,783
[45] Date of Patent: Aug. 30, 1988

[54] GALLSTONE DISSOLVER

[75] Inventors: Kenji Hara, Utsunomiya; Jhoshin Okada, Tochigi, all of Japan

[73] Assignee: Kao Corporation, Tokyo, Japan

[21] Appl. No.: 896,319

[22] Filed: Aug. 13, 1986

Related U.S. Application Data

[63] Continuation of Ser. No. 640,122, Aug. 13, 1984, abandoned.

[30] Foreign Application Priority Data

Aug. 19, 1983 [JP] Japan .................................. 58-151418
Feb. 17, 1984 [JP] Japan .................................. 59-28168
Feb. 17, 1984 [JP] Japan .................................. 59-28171

[51] Int. Cl.$^4$ ..................... A61K 31/22; A61K 31/23; A61K 31/015
[52] U.S. Cl. .................................. 514/546; 514/552; 514/690; 514/703; 514/729; 514/763; 514/766; 514/877
[58] Field of Search ............... 514/690, 552, 546, 703, 514/729, 763, 766, 877

[56] References Cited

U.S. PATENT DOCUMENTS

| | | |
|---|---|---|
| 3,450,819 | 6/1969 | Babayan et al. ................ 514/546 X |
| 3,882,248 | 5/1975 | Igimi et al. .......................... 514/690 |
| 4,205,086 | 5/1980 | Babayan et al. .................... 514/552 |

*Primary Examiner*—Leonard Schenkman
*Attorney, Agent, or Firm*—Oblon, Fisher, Spivak, McClelland & Maier

[57] ABSTRACT

A gallstone dissolver comprises the following active ingredients (A) and (B);

(A) a compound selected from the group consisting of fatty acid monoglycerides of C-6 to C-12, fatty acid diglycerides in liquid phase at 30° C., fatty acid triglycerides in liquid phase at 30° C., and fatty acids in liquid phase at 30° C., and (B) a monoterpene.

The coexistence of the fatty acid and monoterpene in the gallstone dissolver accelerates the sulubility and dissolving velocity of cholesterol gallstones.

A nonionic surfactant such as a polyoxyethylene sorbitan fatty acid ester, glycerin fatty acid ester, etc. may also be added to the above dissolver to further improve the performance of the dissolver.

10 Claims, 7 Drawing Sheets

GALLSTONE DISSOLVER

This application is a continuation of application Ser. No. 640,122, filed Aug. 13, 1984, now abandoned.

BACKGROUND OF THE INVENTION

This invention relates to a novel gallstone dissolver.

There are several types of gallstones, among which cholesterol gallstones, bilirubin gallstones and rare-stones are well known. In Japan, the incidence of cholesterol gallstones has increased due to the recent change of Japanese food life, and reached to about 85% of the total cases of cholelithasis.

The treatments for cholelithasis are roughly classified into two groups which respectively include the surgery treatment by operation and the internal treatment by drugs, but it is advisable to treat a patient by dissolving gallstones internally as much as possible so as to avoid the agony of the patient.

However, the internal treatment currently applicable to patients suffered from cholesterol gallstones are not definitive. Those treatments using chenodeoxycholic acid and ursodeoxycholic acid have the defects of long term administration and low effectiveness rate.

As for the cholesterol gallstones remaining after operation, direct dissolvers were proposed, which include sodium cholate, heparin and d-limonene, but the results were not yet satisfactory. Namely, the solubilities of sodium cholate and heparin are in quite a low level with slow dissolving velocities, thus actually the clinical applications of these compounds were impossible. The solubility and dissolving velocity of d-limonene is better than those of the formers, but complete dissolution in the bile duct were seldomly observed during the clinical process on its administration. Further, d-limonene is defective in that it is stimulative to a patient and requires a special catheter insoluble in d-limonene.

SUMMARY OF THE INVENTION

The inventors have investigated the activities of various compounds for many years to mitigate the above defects of monoterpenses, increase the solubility and dissolving velocity thereof, thereby preparing a gallstone dissolver which may directly dissolve gallstones by applying it endoscopically. Finally, the inventors found that incorporation of monoterpene with a special fatty acid or its glycerin derivative may directly dissolve gallstones with quite low stimulation, and completed the present invention.

Accordingly, the present invention provides a first invention relative to a gallstone dissolver which comprises the following ingredients (A) and (B);
(A) a compound selected from the group consisting of fatty acid monoglycerides of C-6 to C-12, fatty acid diglycerides in liquid phase at 30° C., fatty acid triglycerides in liquid phase at 30° C., and fatty acids in liquid phase at 30° C.,
(B) a monoterpene,
and a second invention relative to a gallstone dissolver including a nonion surfactant in addition to the above two ingredients.

DETAILED DESCRIPTION OF THE INVENTION AND PREFERRED EMBODIMENTS

Figure 1:
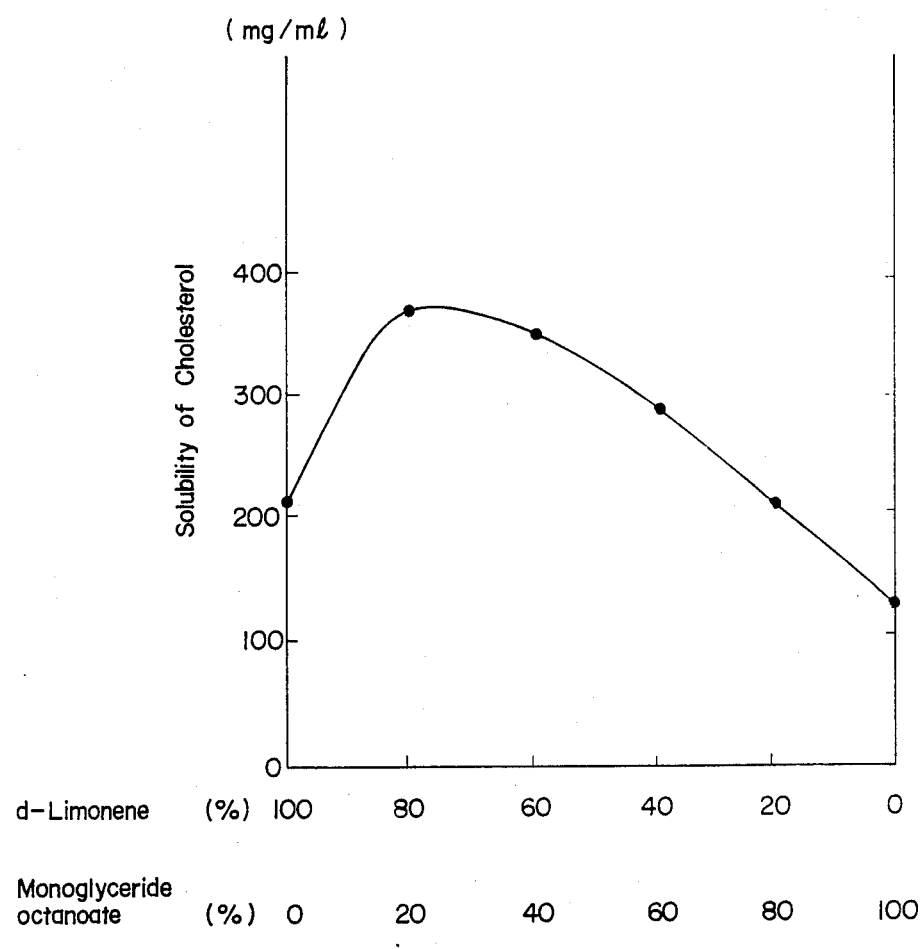
FIG. 1 is a cholesterol solubility curve in the solutions of d-limonene and monoglyceride caprylate.

Among (A) ingredients in the present invention, fatty acid monoglycerides of C-6 to C-12 include, for example, monoglyceride hexanoate (caproate), monoglyceride heptanoate (enanthate), monoglyceride octanoate (caprylate), monoglyceride nonanoate (pelargonate), monoglyceride decanoate (caprate), monoglyceride undecanoate (undecylenate), monoglyceride dodecanoate (laurate), etc., and especially monoglyceride caprylate and monoglyceride caprate are preferable. Fatty acid monoglycerides in liquid phase at ° C. include tributyrin (4, 4, 4), tricaproin (6, 6, 6), tricaprylin (8, 8, 8), 1-caproyl-2,3-diolein (6, 18′, 18′), 1-elaido-2,3-dicaprylin (8, 8, 18′), 1-linoleo-2,3-dicaprylin (8, 8, 18″), 1-caprylyl-2,3-diolein(8, 18′, 18′), trinonanoin (9, 9, 9), tricaprin (10, 10, 10), 1-lauro-2,3-dicaprin(10, 10, 12), 1-myristo-2,3-dicaprin (10, 10, 14), 1-oleo-2,3-dicaprin (10, 10 18′), 1-elaido-2,3-dicaprin (10, 10, 18′), 1-linoleo-2,3-dicaprin (10, 10, 18″), 2-oleo-1,3-dicaprin (10, 18′, 10), 1-capryl-2,3-diolein (10, 18′, 18′), 1- capryl-2,3-dielaidin (10, 18′, 18′), 1oleo-2,3-dilaurin (12,12 18′), 1-elaidino-2,3-dilaurin (12, 12, 18′), 1-linoleo-2,3-dilaurin (12, 12, 18″), 2-oleo-1,3-dilaurin (12, 18′, 12), 1-lauro-2,3-diolein (12, 18′, 18′), 1-lauro-2,3-dilinolein (12, 18″, 18″), 1oleo-2,3-dimyristin (14, 14, 18′), 1-linoleo-2,3-dimyristin (14, 14, 18″), 1-myristo-2,3-diolein (14, 18′, 18′), 1-myristo-2,3-dilinolein (14, 18″, 18″), 1-palmito-2,3-diolein (16, 18′, 18′), 1-palmito-2,3-dilinolein (16, 18″, 18″), 1-stearo-2,3-diolein (18, 18′, 18′), 1-stearo-2,3-dilinolein (18, 18″, 18″), trilinolein (18′, 18′, 18′) trilinolein (18″, 18″, 18″), 2-stearo-1,3-diolein (18′, 18, 18′) etc., among which tricaprylin (triglyceride caprylate) and tricaprin (triglyceride caprate) are especially preferable.

In addition, as fatty acid diglycerides which are liquid at 30° C., 1,2-dioctanoin (diglyceride caprylate), 1,2-dicaprin (diglyceride caprate) and 1,2-dilaurin (diglyceride laurate) are preferable.

Furthermore, fatty acids which are liquid at 30° C. include straight chain saturated fatty acids such as hexanoic acid, heptanoic acid, octanoic acid and nonanoic acid; bifurcate saturated fatty acids such as 2-ethyl hexanoic acid, isocaproic acid, 2-methyl undecanoic acid, 3-methyl docosanoic acid, 2,2-methyl dodecanoic acid, methyl tetradecanoic acid, 2-ethyl tetradecanoic acid, 2-propyl tridecanoic acid, 2-butyl dodecanoic acid, 2-pentyl undecanoic acid, 2-heptyl nonanoic acid, 2, 3-dimethyl tetradecanoic acid, 2-ethyl hexadecanoic acid, 2-heptyl undecanoic acid, 2-butyl tetradecanoic acid, isostearic acid, Emery type isostearic acid, etc.; straight chain monoen fatty acids such as 3-hexenoic acid, 4-hexenoic acid, 6-heptenoic acid, 3-octenoic acid, 2-decenoic acid, 4-decenoic acid, 9-undecenoic acid, 10-undecenoic acid, 3-decenoic acid, cis-9-tridecenoic acid, 4-tetradecenoic acid, cis-9-hexadecenoic acid, cis- 7-heptadecenoic acid, cis-8-heptadecenoic acid, cis-9-heptadecenoic acid, cis-7-octadecenoic acid, cis-8-octadecenoic acid, cis-9-nonadecenoic acid, cis-11-eicosenoic acid etc.; bifurcate monoen fatty acids such as trans-2-methyl-2-pentenoic acid, cis-2-methyl 2hexanoic acid, 2methylene hexanoic acid, meta acrylic acid, 2-ethyl hexanoic acid, 3-methyl-2-nonenoic acid, 3-methyl-3nonenoic acid, L(+)-2,4-dimethyl-2-dodecenoic acid etc.; di-, tri- or tetra-en fatty acids such as linolic acid, trans-10, cis-12-octadecadienoic acid, cis-9, cis-11-octadecadienoic acid, linolenic acid, arachidonic acid, etc.; and acetylene fatty acids such as 2-hexinic acid, 2-heptinic acid, 2-octinic acid, 7-octinic acid, 2-noninic acid, 2-decinic acid, 6-undecinic acid, 6-dodecinic acid, 7-dodecinic acid, 6-tridecinic acid, 8-tridecinic acid, etc., among which, linolic acid, linolenic acid, Emery type isostearic acid, 2-ethyl hexanoic acid and isocaproic acid are especially preferable.

Monoterpenes as (B) ingredients of the present invention include myrcene, ocimene, limonene, pinene, linalool, geraniol, nerol, citronellol, citral, citronellal, dipentine, terpineol, phellandrene, terpinene, sylvestrene, terpinolene, perilaldehyde, carvone, menthone, piperitenone, cineol etc., among which especially limonene and menthone are preferable.

Among (A) ingredients in the present invention, either one of fatty acid monoglycerides, fatty acid diglycerides or fatty acid triglycerides is conventionally used as a food emulsifier, a cooking oil or a food additive with low toxicity. Fatty acids are also hypotoxic and found in natural foods. Monoterpenes of (B) ingredients are safe compounds as will be understood from the low toxicity of d-limonene, $LD_{50}$ of which is 4.5g/kg. Consequently, the toxicities of gallstone dissolvers according to the present invention are extremely low; for example, 25g/kg for d-limonene-monoglyceride caprylate (60:40), 33g/kg for d-limonene-monoglyceride caprylate (40:60), 27g/kg for d-limonene-triglyceride caprylate (60:40), 38g/kg for d-limonene-triglyceride caprylate (40:60), 24g/kg for d-limonene-linolic acid (60:40) and 31g/kg for d-limonene-linolic acid (40:60).

It is desirable to prepare a gallstone dissolver in a proportion of (A) ingredient 20 to 70 volume percent (hereinafter described simply as %) to (B) ingredient 80 to 30%. A more excellent effect will be obtainable by using a nonionic surfactant as a (C) ingredient together with the above two active ingredients. Nonionic surfactants include sorbitan fatty acid esters such as sorbitan monolaurate, sorbitan monopalmitate, sorbitan monostearate, sorbitan sesquistearate, sorbitan tristearate, sorbitan monooleate, sorbitan sesquioleate, and sorbitan trioleate; polyoxyethylene sorbitan fatty acid esters such as polyoxyethylene sorbitan monolaurate, polyoxyethylene sorbitan monopalmitate, polyoxyethylene sorbitan monostearate and polyoxyethylene sorbitan monooleate; glycerin fatty acid esters such as coconut oil fatty acid ester, glycerin monostearate and glycerin monooleate; polyoxyethylene alkyl ethers such as polyoxyethylene oleyl ether; polyoxyethylene hardened castor oil derivatives; sugar fatty acid esters; polyethylene glycol fatty acid esters such as polyethylene glycol stearate; polyoxyethylene sugar fatty acid esters, etc. As regards the effectiveness, sorbitan fatty acid esters, polyoxyethylene sorbitan fatty acid esters (20 moles in average of ethyleneoxide being added) and polyoxyethylene hardened castor oil derivatives (60 moles in average of ethyleneoxide being added) are especially preferable.

In order to obtain a more excellent effect of a (C) ingredient, it is preferable to compound it in a proportion of 0.5% or more, and more preferably 1.0 to 3.0% of the total ingredient.

The mechanism of the activity of a gallstone dissolver in the present invention is not completely solved, but it is considered that the coexistence of said fatty acid and monoterpene accelerates the solubility and dissolving velocity of cholesterol gallstones.

A gallstones dissolver in the present invention is usable in a treatment that gallstones remained after operation are dissolved by injecting the gallstone dissolver into the nasocholangio-drain indwelled after endoscopic thelectomy, or in a non-wet treatment that gallstones are directly dissolved by injecting the gallstone dissolver into the nasocholangio-drain.

The dosage of a gallstone dissolver according to the present invention depends upon age and symptom of patients. It is preferable, however, to administer 50 to 100 ml/day by drain-injection during 2 to 10 hours a day at the velocity of 3 to 10 ml/hr for 3 to 14 days — usually 4 to 10 days.

The invention will be further described by way of Examples.

EXAMPLE 1

The solubilities of anhydrous cholesterol against the solutions of monoglyceride caprylate and dlimonene in various proportions therebetween were determined at 37° C. As shown in FIG. 1, the solutions of monoglyceride caprylate and d-limonene in which is contained 20 to 70% of monoglyceride caprylate showed considerably higher solubilities compared with that at single application of each ingredient. The determination of cholesterol was carried out by the ferric chloride-sulfuric acid chromatogram using Kiliani reaction.

EXAMPLE 2

Figure 2:
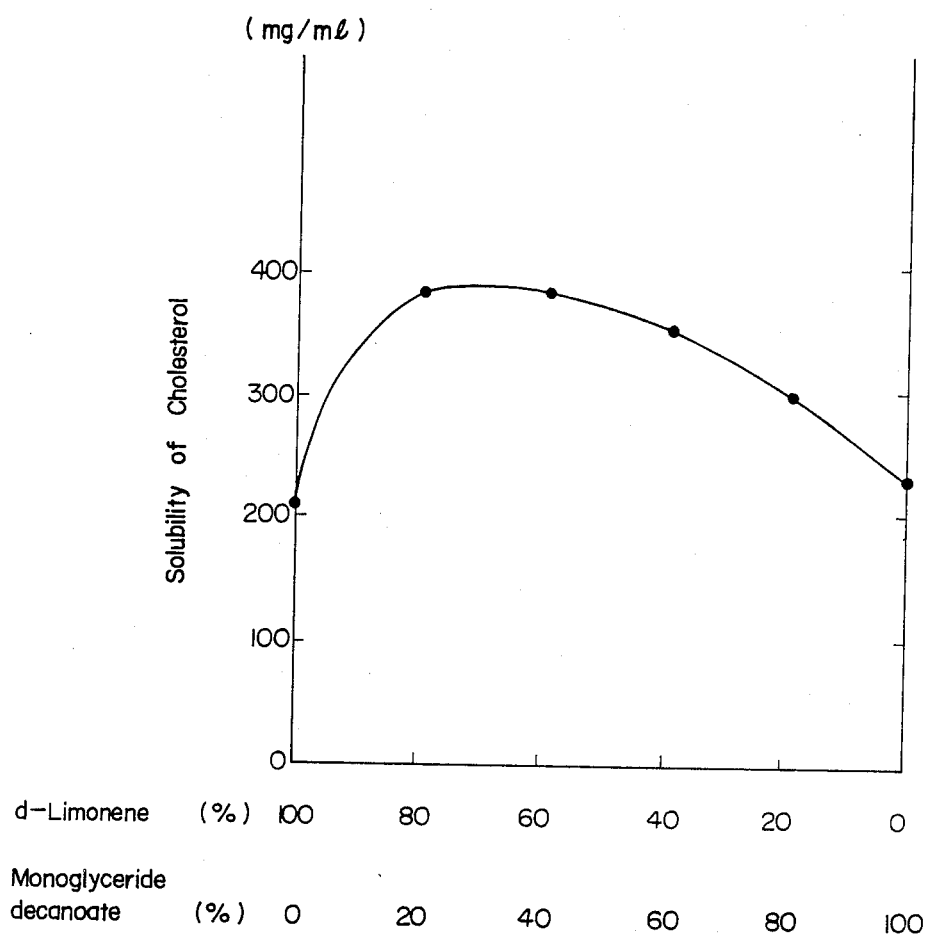
FIG. 2 is a cholesterol solubility curve in the solutions of d-limonene and monoglyceride decanoate.

Example 1 was repeated replacing monoglyceride caprylate with monoglyceride caprate, and the solubilities of anhydrous cholesterol against the solutions of monoglyceride caprate and d-limonene in various proportions therebetween were determined at 37° C. The results are shown in FIG. 2.

EXAMPLE 3

Figure 3:
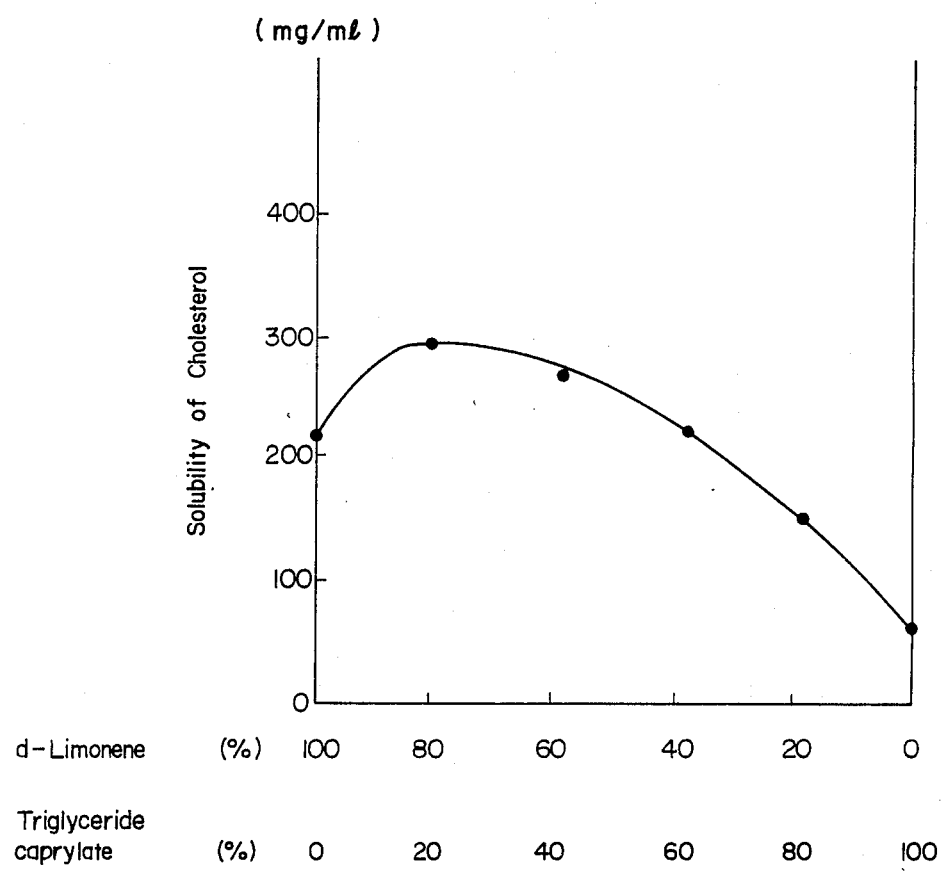
FIG. 3 is a cholesterol solubility curve in the solutions of d-limonene and trigylceride caprylate.

In the same manner as Example 1, the solubilities of anhydrous cholesterol against the solutions of triglyceride caprylate and d-limonene in various proportions therebetween were determined at 37° C. As shown in FIG. 3, the two component system of triglyceride caprylate and d-limonene showed considerably higher solubilities when triglyceride caprylate is contained 20 to 70% compared with that at single application of each ingredient.

EXAMPLE 4

Figure 4:
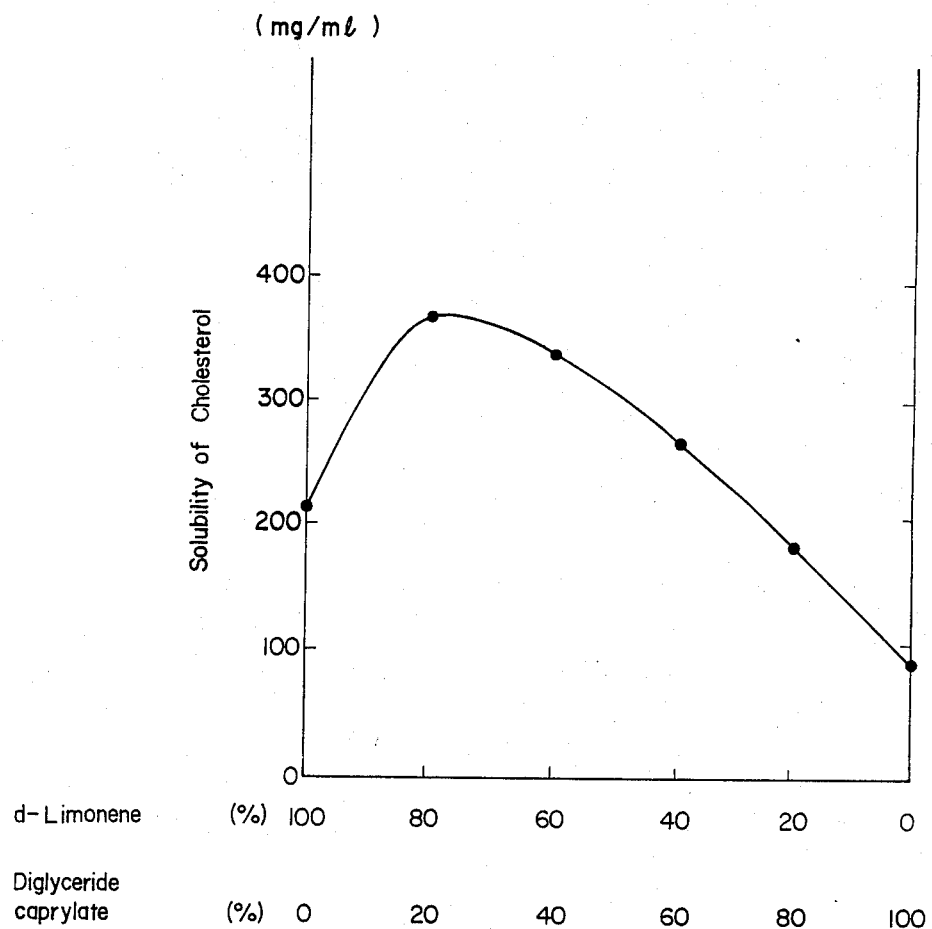
FIG. 4 is a cholesterol solubility curve in the solutions of d-limonene and diglyceride caprylate.

In the same manner as Example 1, the solubilities of anhydrous cholesterol against the solutions of diglyceride caprylate and d-limonene in various proportions therebetween were determined. As shown in FIG. 4, the two component system of diglyceride caprylate and d-limonene showed considerably higher solubilities when diglyceride caprylate is contained 20 to 70% compared with that at single application of each ingredient.

EXAMPLE 5

Figure 5:
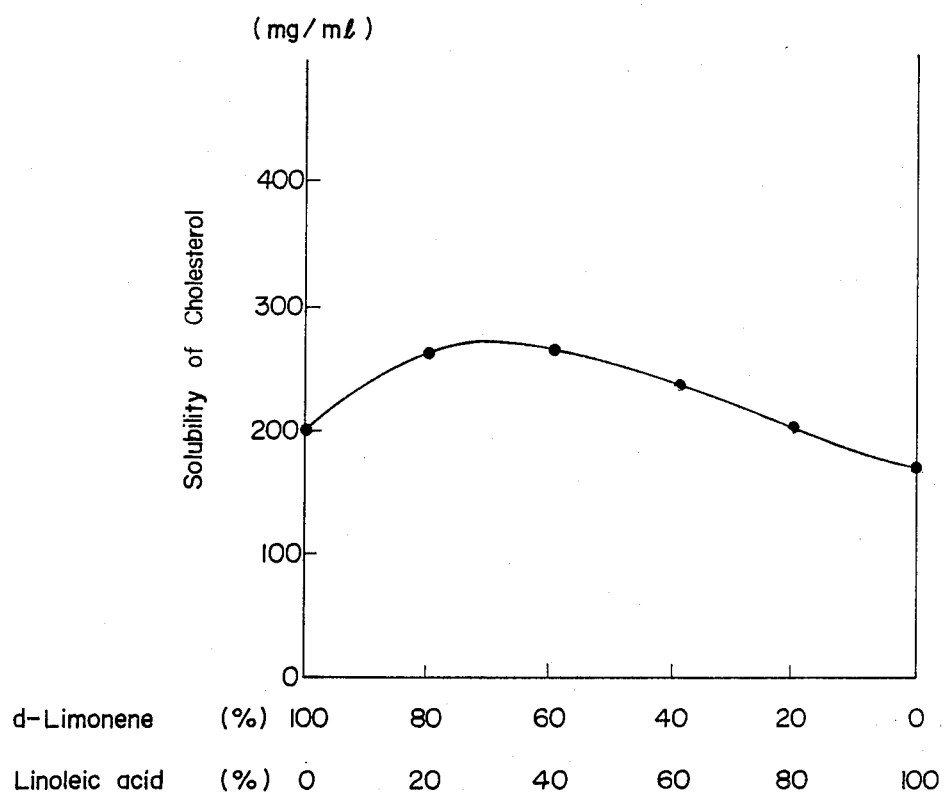
FIG. 5 is a cholesterol solubility curve in the solutions of d-limonene and linolic acid.

In the same manner as Example 1, the solubilities of anhydrous cholesterol against the solutions of linolic acid and d-limonene in various proportions therebetween were determined. As shown in FIG. 5, the two component system of linolic acid and d-limonene showed considerably higher solubilities when linolic acid is contained 20 to 70% compared with that at single application of each ingredient.

EXAMPLE 6 d-Limonene of 60ml was added to sorbitan monooleate of 1.5 g, and completely mixed in a warm bath at 50° C. Monoglyceride caprylate, triglyceride caprylate and linolic acid were added respectively to the said mixture to make the total volume 100ml. After each solution was allowed to stand at 5° C. for 1 day, the solution was filtered. The filtered solution was found to be stable for a long period at 5° C.

The same results were obtained for the cases of sorbitan monooleate replaced with noionic surfactant such as sorbitan monolaurate, glyceryl monostearate, sorbitan monopalmitate, polyoxyethylene sorbitan monooleate and polyoxyethylene tristearate, for the case of monoglyceride caprylate replaced with monoglyceride caprate, and for the case of triglyceride caprylate replaced with triglyceride caprate.

EXAMPLE 7

Figure 6:
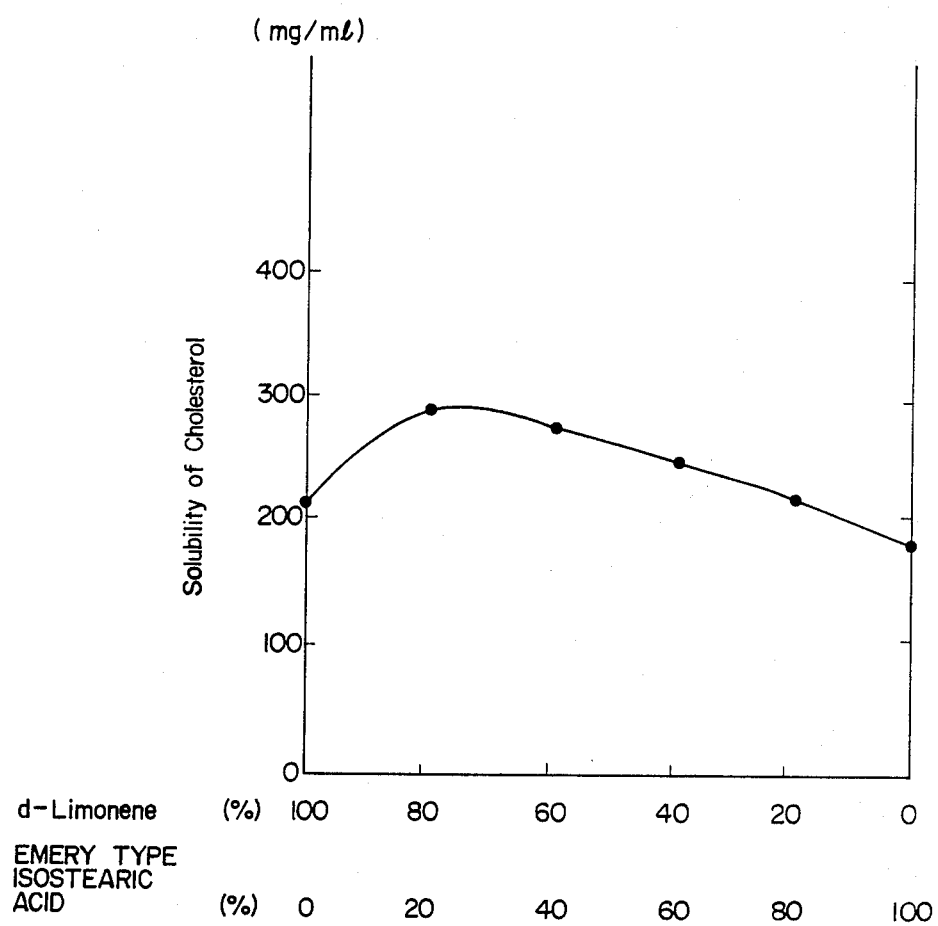
FIG. 6 is a cholesterol solubility curve in the solutions of d-limonene and Emery type isostearic

The solubilities of anhydrous cholesterol against the solutions in various proportions of Emery type isostearic acid* and d-limonene were determined in the same manner as in Example 1. As shown in FIG. 6, the two component system of Emery type isostearic acid and d-limonene showed considerably higher solubilities when Emery type isostearic acid is contained 20 to 70% compared with that at single application of each ingredient.

*Emery type isostearic acid

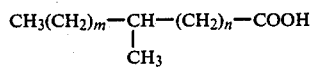

(In the formula, the sum of m and n is 14, and the distribution appears around m=n=7.)

EXAMPLE 8 d-Limonene of 60 ml was added to sorbitan monolaurate of 2.0 g. After completely mixed up in a warm bath at 50° C., Emery type isostearic acid was added to make the total volume 100 ml. The solution was allowed to stand for 1 day at 5° C., followed by filtration. The filtered solution was found to be stable for a long period at 5° C.

The same results were obtained in the cases of sorbitan monolaurate replaced with nonionic surfactants including sorbitan monooleate, glyceryl monostearate, sorbitan monopalmitate, polyoxyethylene sorbitan monooleate and polyoxyethylene tristearate.

EXAMPLE 9

The dissolving velocities of 1 g artificial cholesterol gallstone (a cylindrical tablet of 10 mm in diameter × 12 mm high made with French Press at 50 Kg/cm$^2$) in a 50 ml solvent were determined by the revolving basket method at 25 r.p.m. using the U.S.P. elution tester. The results are shown in Table 1.

TABLE 1

| Composition | d-Limonene (%) | 100 | 80 | 60 | 40 | 20 | 0 |
|---|---|---|---|---|---|---|---|
| | Monoglyceride Caprylate (%) | 0 | 20 | 40 | 60 | 80 | 100 |
| Time to dissolve completely 1 g of artificial cholesterol gallstone (hour) | | 1.7 | 3.75 | 6.5 | 10 | 33 | 120 |

EXAMPLE 10

Each of 2.0 ml solutions of d-limonene and monogylceride caprylate in the following proportions therebetween was intra-abdominally administered to a male SD rat weighing about 250 g. The rat was killed by vertebral dislocation 30 min after administration. The intra-abdominal condition, especially in the small intestine was observed by ventrotomy. The criterion was dependent on 4 degrees of congestion and edema. The results are shown in Table 2.

TABLE 2

| Composition | d-Limonene (%) | 100 | 80 | 60 | 40 | 20 | 0 |
|---|---|---|---|---|---|---|---|
| | Monoglyceride Caprylate (%) | 0 | 20 | 40 | 60 | 80 | 100 |
| Congestion | | ++ | + | ± | − | − | − |
| Edema | | + | + | ± | − | − | − |

Criterion
−: Not found.
±: Scarcely observed.
+: Slightly observed.
++: Significantly observed.

As shown in Table 2, sole use of d-limonene produced congestion and edema in the small intestine showing strong stimulativity of d-limonene, but mixtures of d-limonene and monoglyceride caprylate scarcely produced congestion or edema showing very reduced stimulation.

EXAMPLE 11

In the same manner as Example 10, congestion and edema in the small intestine resulted from administration of each 2.0 ml solution of d-limonene and triglyceride caprylate were observed. The results are shown in Table 3.

TABLE 3

| Composition | d-Limonene (%) | 100 | 80 | 60 | 40 | 20 | 0 |
|---|---|---|---|---|---|---|---|
| | Triglyceride Caprylate (%) | 0 | 20 | 40 | 60 | 80 | 100 |
| Congestion | | ++ | ± | − | − | − | − |
| Edema | | + | ± | − | − | − | − |

According to Table 3, sole use of d-limonene produced congestion and edema in the small intestine showing strong stimulativity of d-limonene, but mixtures of d-limonene and triglyceride caprylate scarcely produced congestion or edema showing very reduced stimulation.

EXAMPLE 12

In the same manner as Example 11, congestion and edema in the small intestine resulted from administration of each 2.0 ml solution of d-limonene and linolic acid were observed. The results are shown in Table 4.

TABLE 4

| Composition | d-Limonene (%) | 100 | 80 | 60 | 40 | 20 | 0 |
|---|---|---|---|---|---|---|---|
| | Linolic Acid Caprylate (%) | 0 | 20 | 40 | 60 | 80 | 100 |
| Congestion | | ++ | + | ± | − | − | − |
| Edema | | + | ± | ± | − | − | − |

According to Table 4, sole use of d-limonene produced congestion and edema in the small intestine showing strong stimulativity of d-limonene, but mixtures of d-limonene and linolic acid scarcely produced congestion or edema showing very reduced stimulation.

EXAMPLE 13

Figure 7:
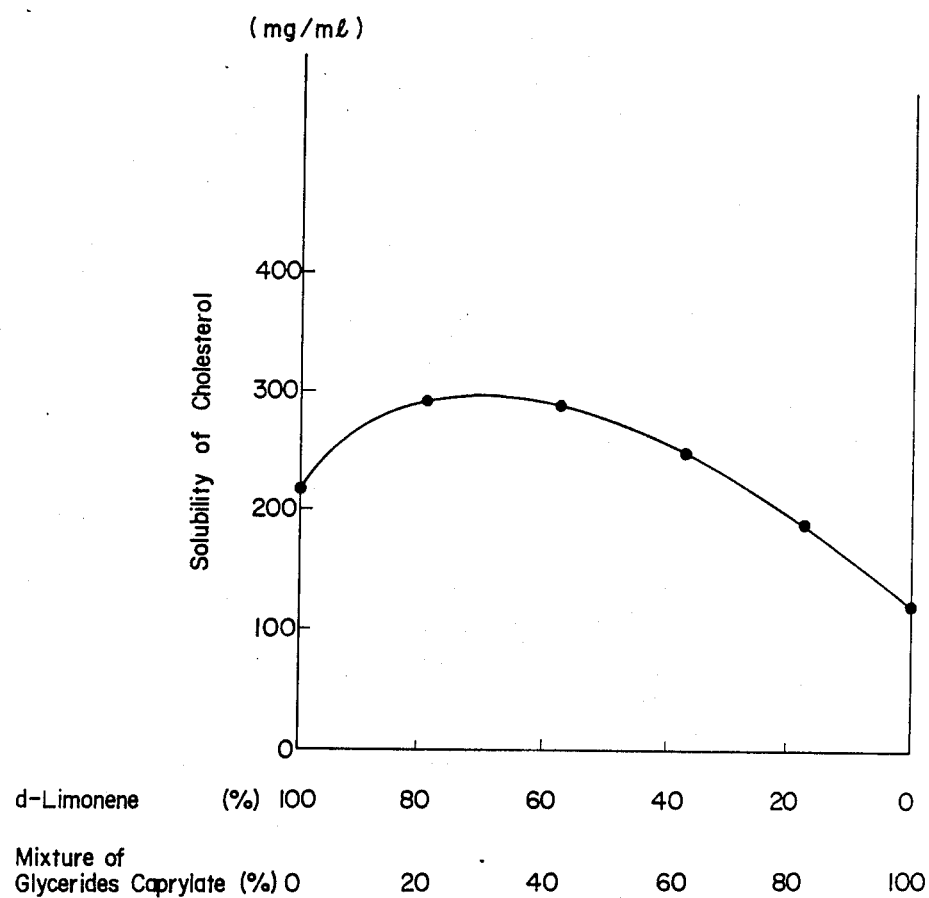
FIG. 7 is a cholesterol solubility curve in the solutions of d-limonene and the mixture of glycerides caprylate.

The solubilities of anhydrous cholesterol against the solutions in various proportions of d-limonene and the mixture of triglyceride caprylate, diglyceride caprylate and monoglyceride caprylate (weight ratio 60 : 8 : 32) were determined at 37° C. The results are shown in FIG. 7. In the two-component system of d-limonene and the mixture of triglylceride caprylate, diglyceride caprylate and monoglyceride caprylate, 10 to 80% of the mixture showed considerably higher solubilities when compared with that at single application of each ingredient. The determination of cholesterol was carried out by the ferric chloridesulfuric acid chromatogram using Kiliani reaction.

What is claimed is:

1. A gallstone dissolver which comprises the following ingredients (A) and (B):
   (A) 20 to 40 percent by volume of a fatty acid monoglyceride selected from the group consisting of monoglyceride hexanoate, monoglyceride heptanoate, monoglyceride octanoate, monoglyceride nonanoate, monoglyceride decanoate, monoglyceride undecanoate, mooglyceride dodecanoate, and
   (B) 80 to 60 percent by volume of a monoterpene selected from the group consisting of limonene, pinene, dipentene, terpineol, phellandrene, perilaldehyde, carvone, and menthone.

2. The gallstone dissolver according to claim 1 in which the ingredient (A) is monoglyceride octanoate or monoglyceride decanoate.

3. The gallstone dissolver according to claim 1 in which the monoterpene of ingredient (B) is limonene or menthone.

4. A gallstone dissolver according to claim 1, wherein said monoterpene is selected from the group consisting of limonene, pinene, terpineol, phellandrene, carvone, and methone.

5. A gallstone dissolver according to claim 1, wherein said monoterpene is selected from the group consisting of menthone, dipentene, terpineol, phellandrene, periladehyde and carvone.

6. A gallstone dissolver according to claim 1, wherein said monoterpene is selected from the group consisting of limonene, menthone, and carvone.

7. A gallstone dissolver which comprises the following ingredients (A), (B) and (C):
   (A) 20 to 40 percent by volume of a fatty acid glyceride selected from the group consisting of monoglyceride hexanoate, monoglyceride heptanoate, monoglyceride octanoate, monoglyceride nonanoate, monoglyceride decanoate, monoglyceride undecanoate, monoglyceride dodecanoate,
   (B) 80 to 60 percent by volume of a monoterpene selected from the group consisting of limonene, pinene, dipentene, terpineol, phellandrene, perilaldehyde, carvone, and menthone, and
   (C) 0.5 to 3 percent by weight of a nonionic surfactant selected from the group consisting of sorbitan monolaurate, sorbitan monopalmitate, sorbitan monostearate, sorbitan sesquistearate, sorbitan tristearate, sorbitan monooleate, sorbitan sesquioleate, sorbitan trioleate, polyoxyethylene sorbitan monolaurate, polyoxyethylene sorbitan monopalmitate, polyoxyethylene sorbitan monostearate, polyoxyethylene sorbitan monooleate, coconut oil fatty acid ester, glycerin monostearate, glycerin monooleate, polyoxyethylene oleyl ether, polyoxyethylene hardened castor oil derivatives 60 moles on average of ethyleneoxide and polyethylene glycol stearate being added.

8. A gallstone dissolver according to claim 7, wherein said monoterpene is selected from the group consisting of limonene, pinene, terpineol, phellandrene, carvone and menthone.

9. A gallstone dissolver according to claim 7, wherein said monterpene is selected from the group consisting of menthone, dipentene, terpineol, phellandrene, periladehyde and carvone.

10. A gallstone dissolver according to claim 7, wherein said monoterpene is selected from the group consisting of limonene, menthone and carvone.

* * * * *